(12) United States Patent
Wong et al.

(10) Patent No.: US 7,933,644 B2
(45) Date of Patent: Apr. 26, 2011

(54) INSTANTANEOUS AUTONOMIC NERVOUS FUNCTION AND CARDIAC PREDICTABILITY BASED ON HEART AND PULSE RATE VARIABILITY ANALYSIS

(75) Inventors: Lid B. Wong, San Diego, CA (US); Donovan B. Yeates, Escondido, CA (US); Guanglin Li, Chicago, IL (US); Tarun Chandra, Gurnee, IL (US); Mahandas A. Kizhakayil, Naperville, IL (US)

(73) Assignee: Cytoptics Corporation, San Marcos, CA (US)

( * ) Notice: Subject to any disclaimer, the term of this patent is extended or adjusted under 35 U.S.C. 154(b) by 1233 days.

(21) Appl. No.: 10/552,009

(22) PCT Filed: Mar. 26, 2004

(86) PCT No.: PCT/US2004/009390
§ 371 (c)(1),
(2), (4) Date: Oct. 10, 2006

(87) PCT Pub. No.: WO2004/086967
PCT Pub. Date: Oct. 14, 2004

(65) Prior Publication Data
US 2007/0219455 A1  Sep. 20, 2007

Related U.S. Application Data

(60) Provisional application No. 60/457,743, filed on Mar. 26, 2003.

(51) Int. Cl.
*A61B 5/04* (2006.01)
(52) U.S. Cl. ...................................... 600/523; 600/509
(58) Field of Classification Search ................... 600/509, 600/523–526
See application file for complete search history.

(56) References Cited

U.S. PATENT DOCUMENTS 5,291,400 A * 3/1994 Gilham ........................ 600/509
5,419,338 A    5/1995 Sarma et al.

* cited by examiner

*Primary Examiner* — Mark W Bockelman
(74) *Attorney, Agent, or Firm* — Schlee IP International, P.C.; Alexander R. Schlee

(57) ABSTRACT

A system and method that can simultaneously acquire electrocardiogram or pulse rate data (42, 44, 46), dynamically perform time-frequency (70) and chaotic analysis (60) in real-time, visually display the results in a convenient graphical format (50) and store the results in a computer file format (50).

11 Claims, 12 Drawing Sheets

Figure 1: Waveform of a conventional heart beat
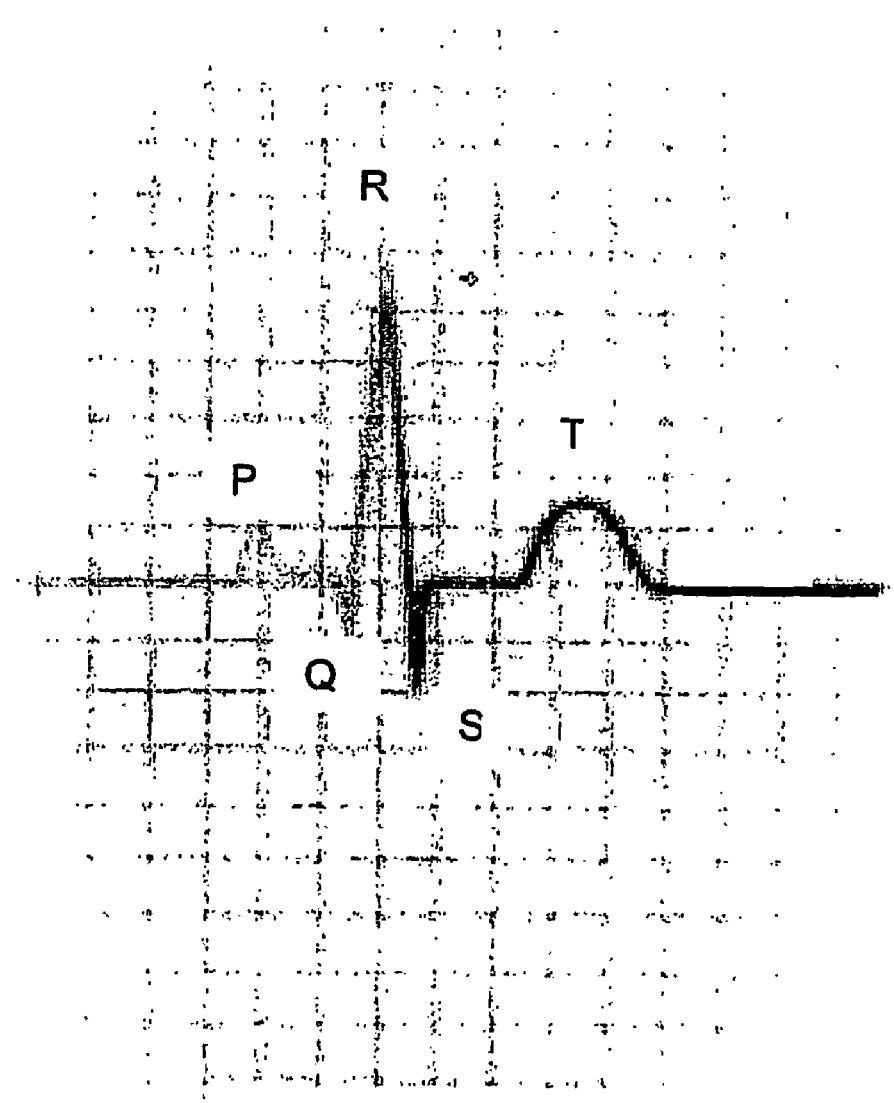

Figure 2: An example of computer and data acquisition device used for the present invention.
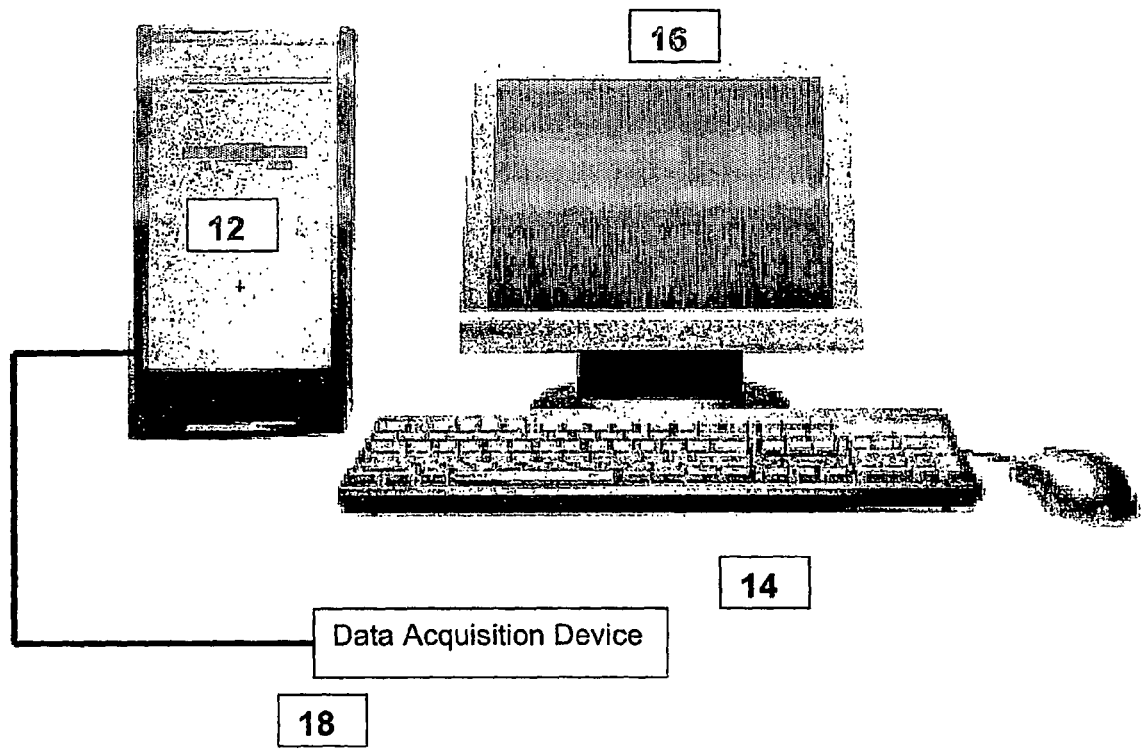

Figure 3: a picture showing the invention with the screenshot from the system performing HRC analysis on pre-acquired representation data from a healthy human.
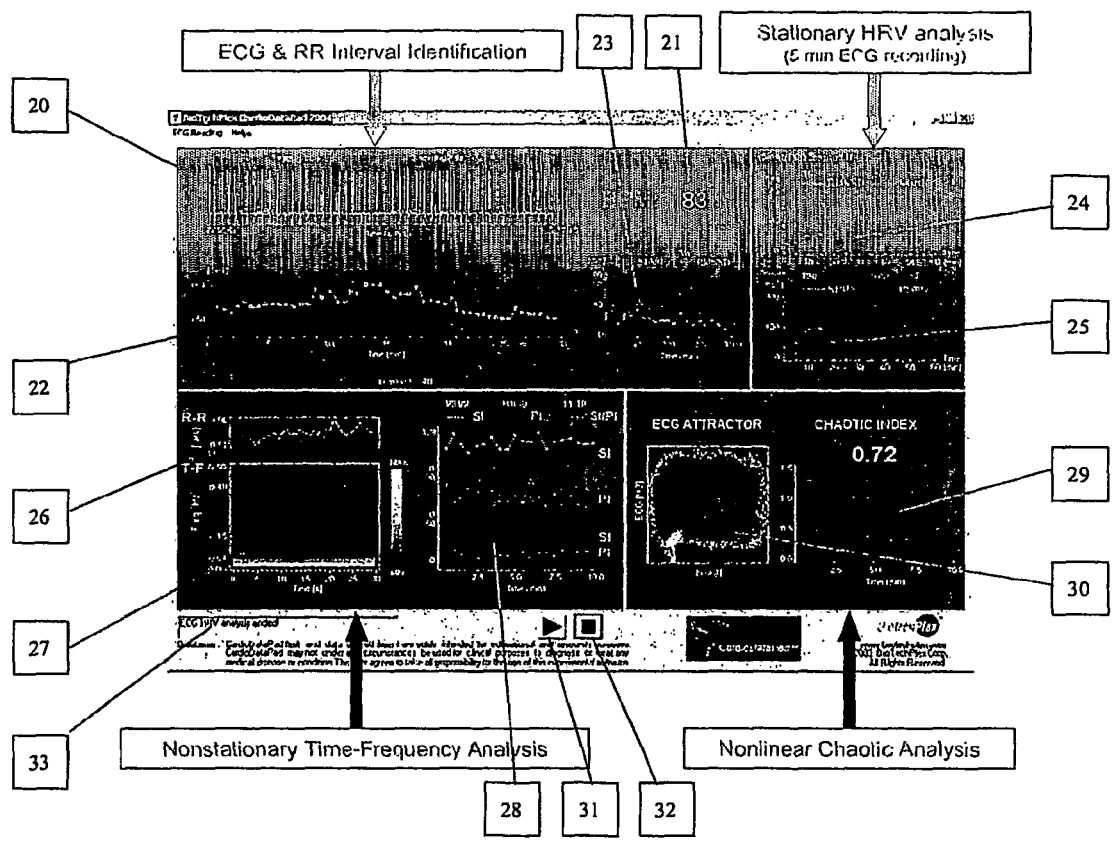

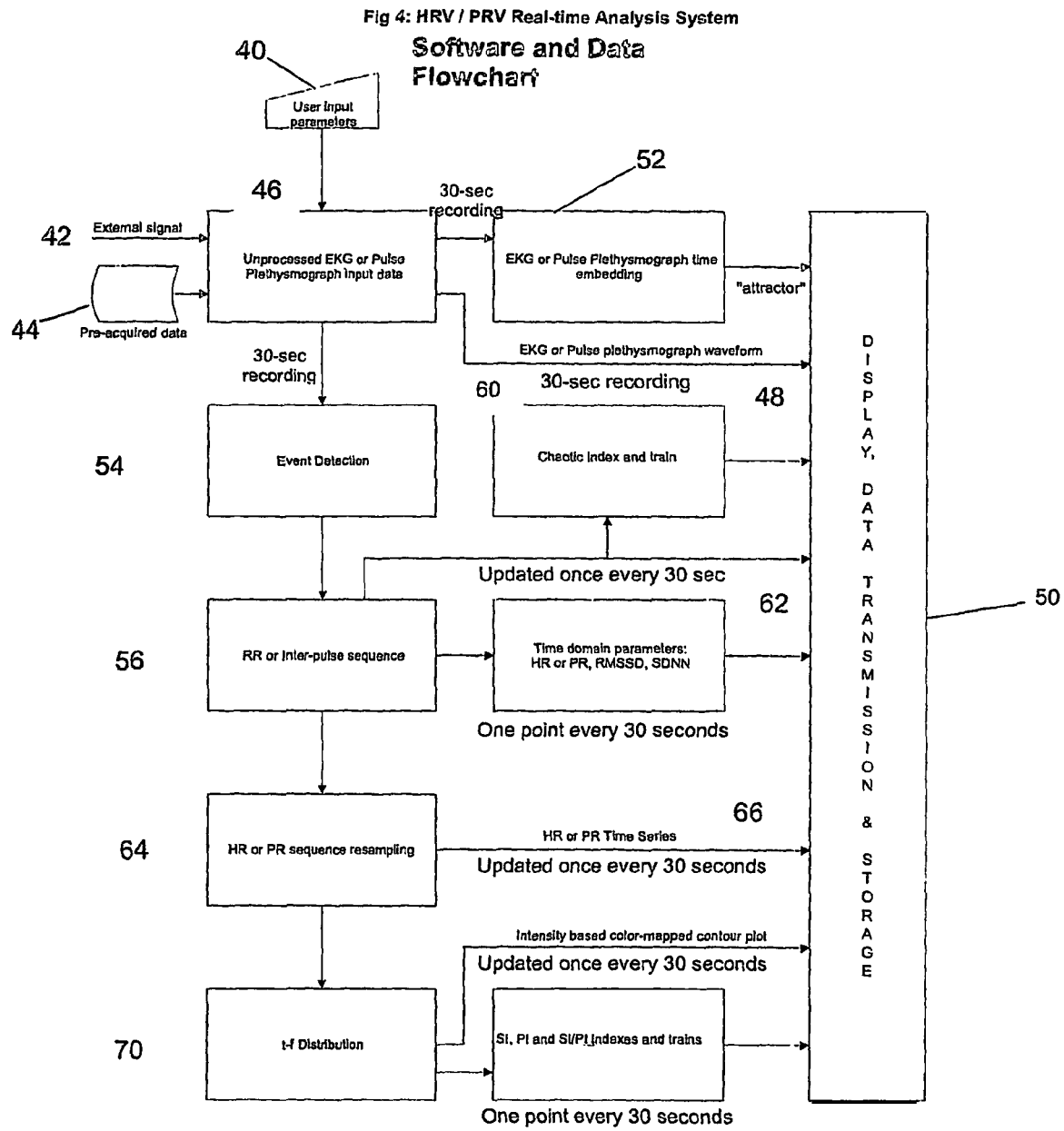

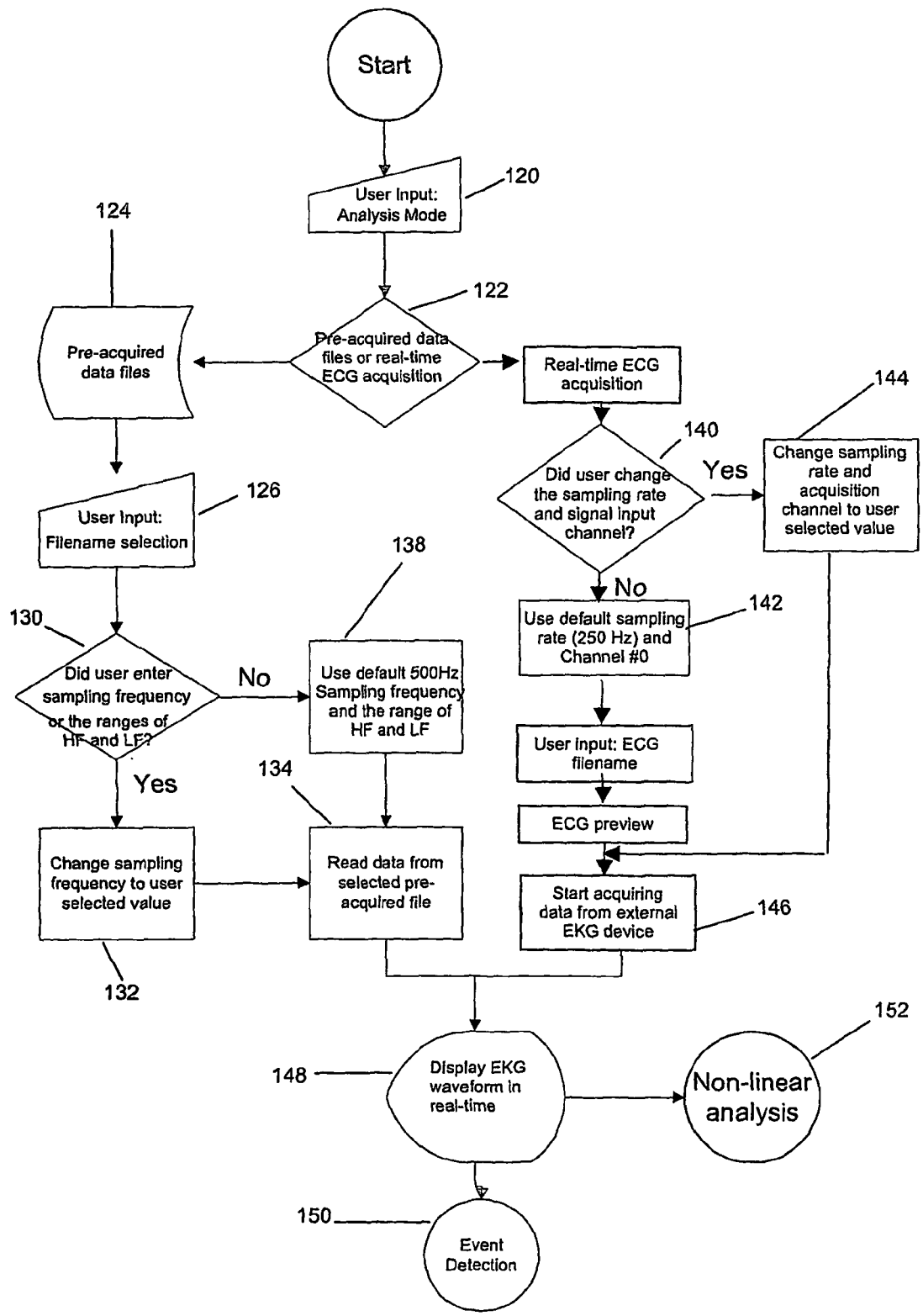

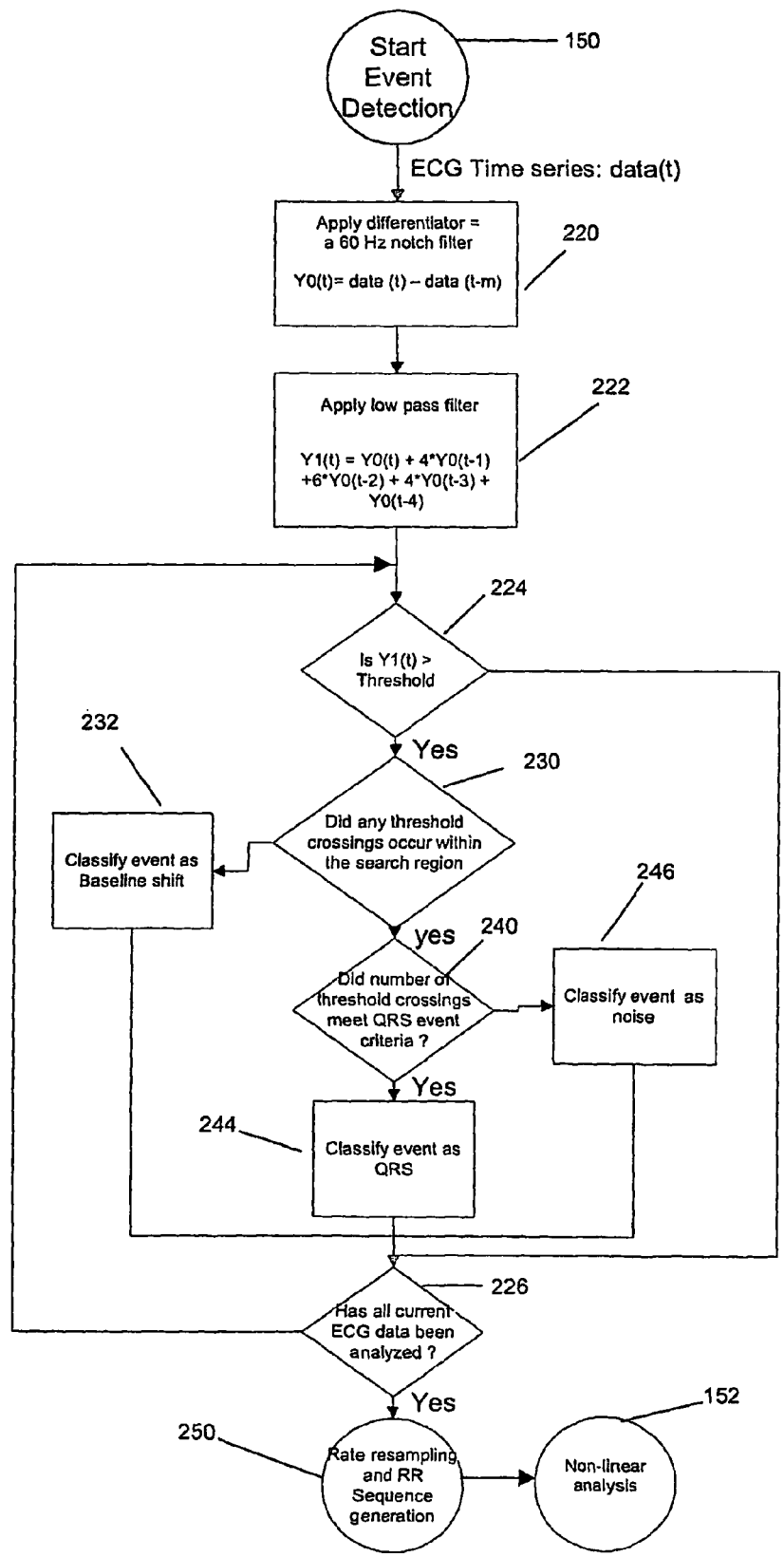
Fig 6: QRS EVENT DETECTION

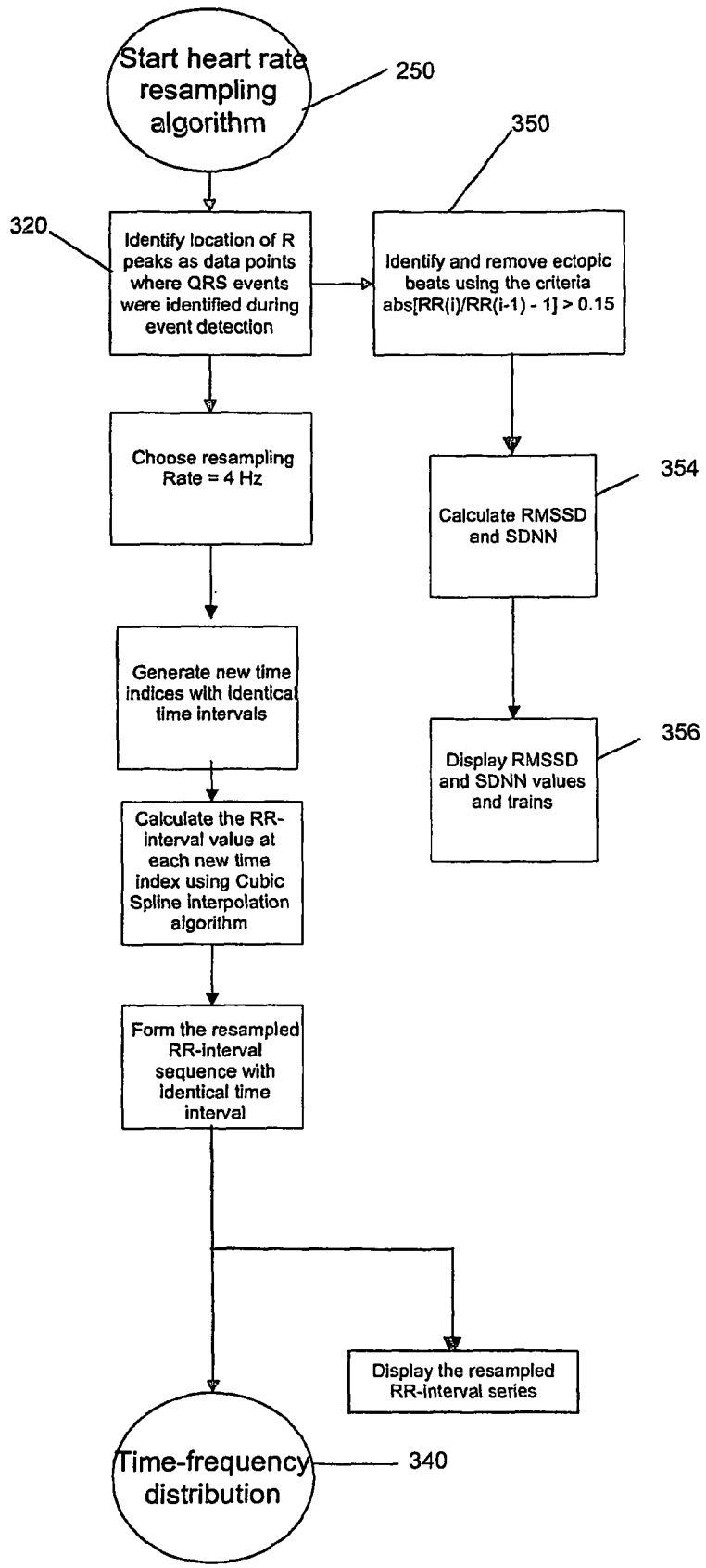

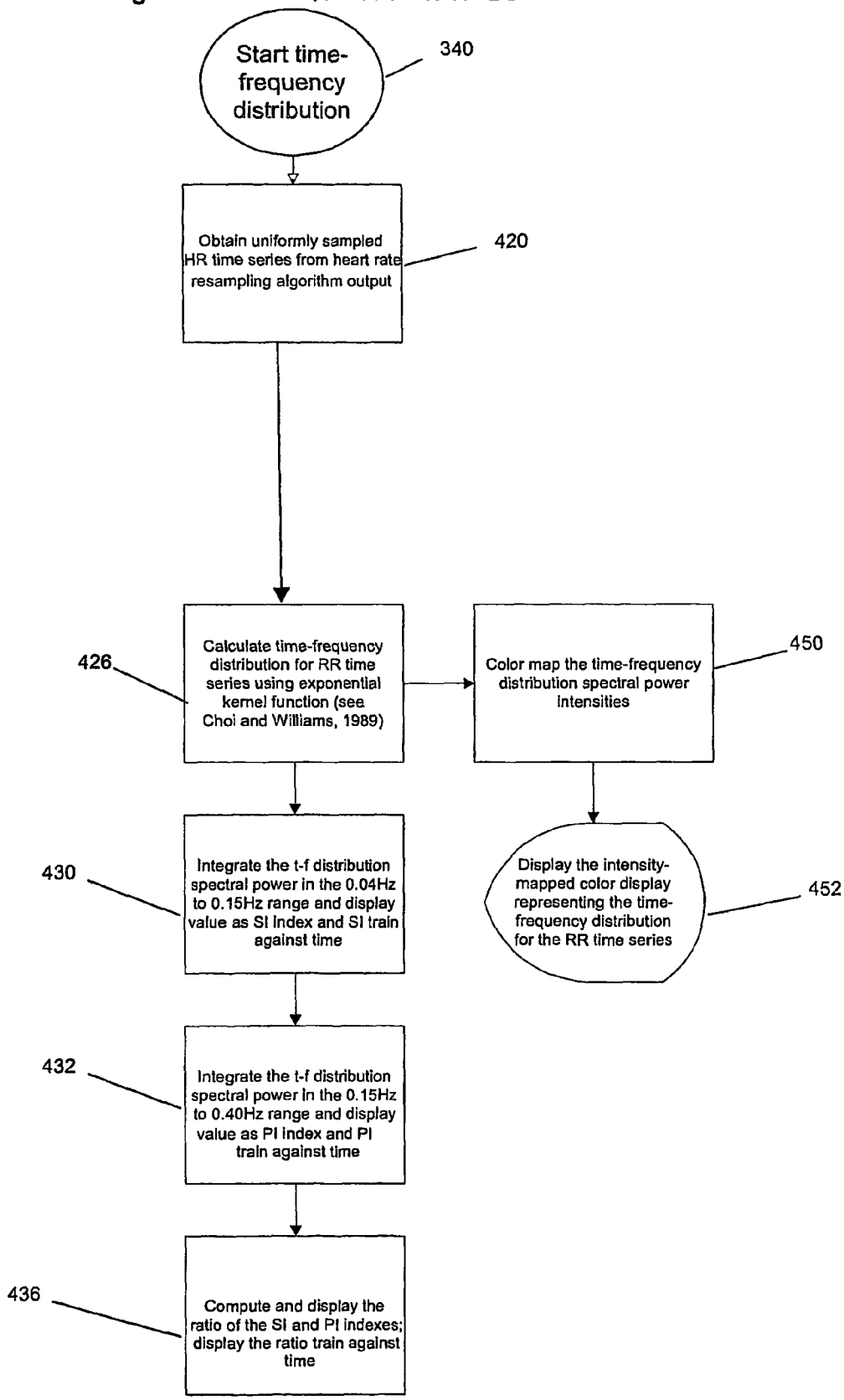
Fig 8: TIME-FREQUENCY DISTRIBUTION

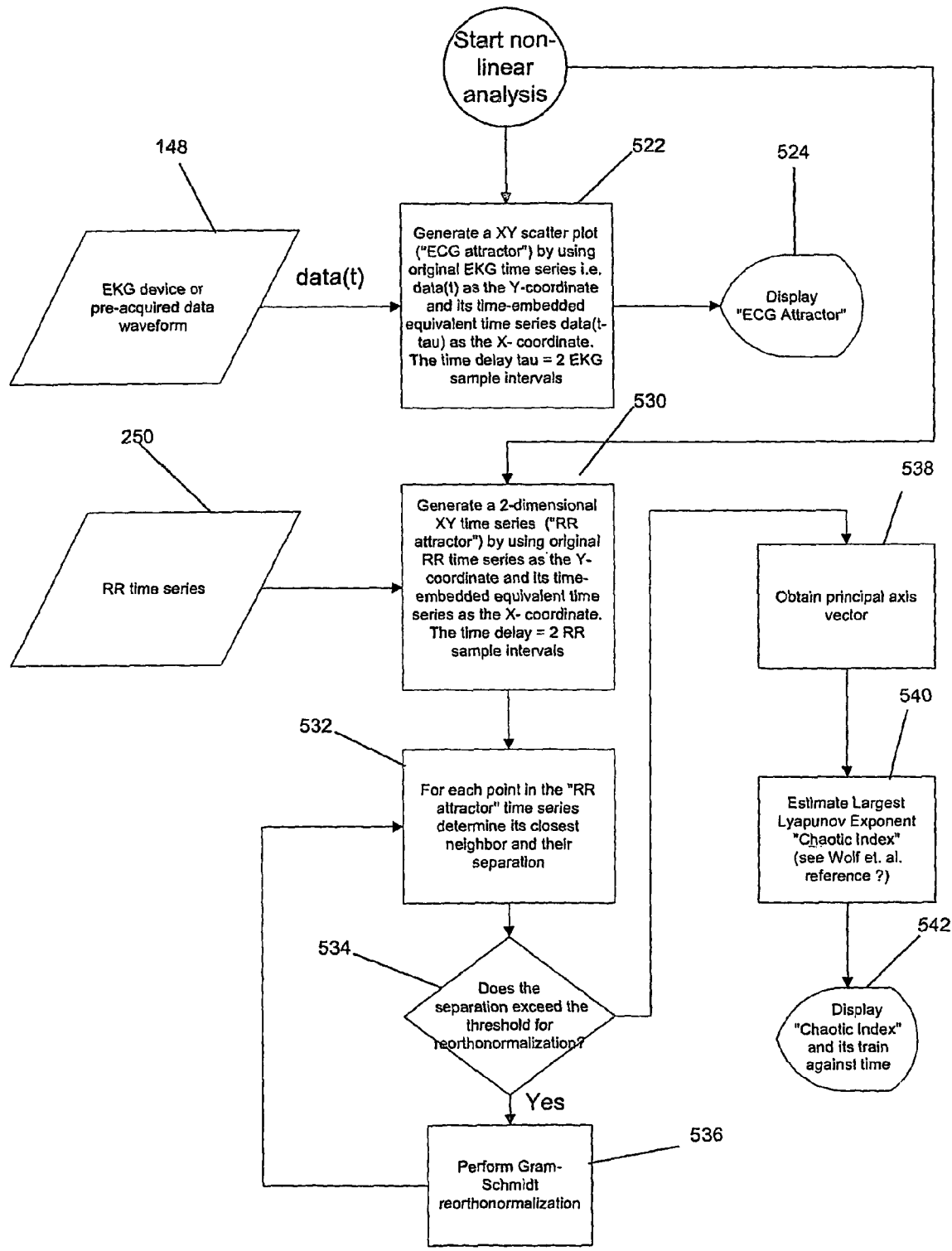

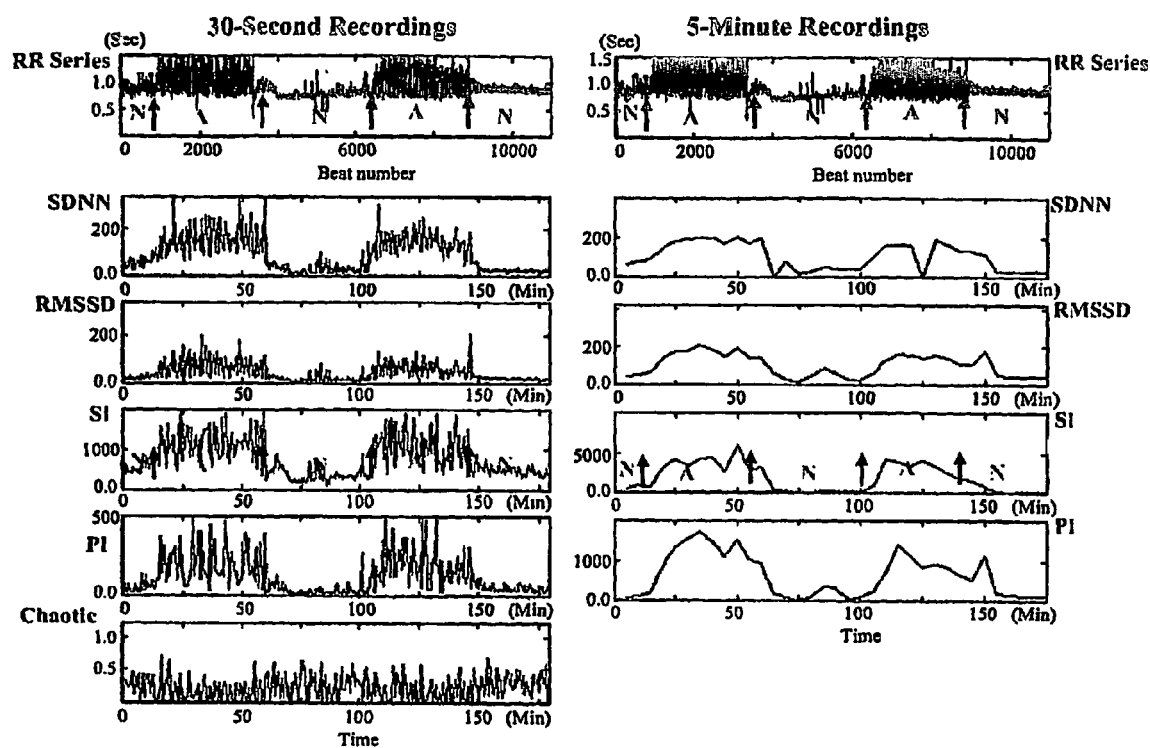
Figure 10: An example of the results analyzed from the system performing HRV analysis on pre-acquired representative data for an electrocardiogram of a human subject with sleep apnea. N denotes normal breathing, A denotes apnea.

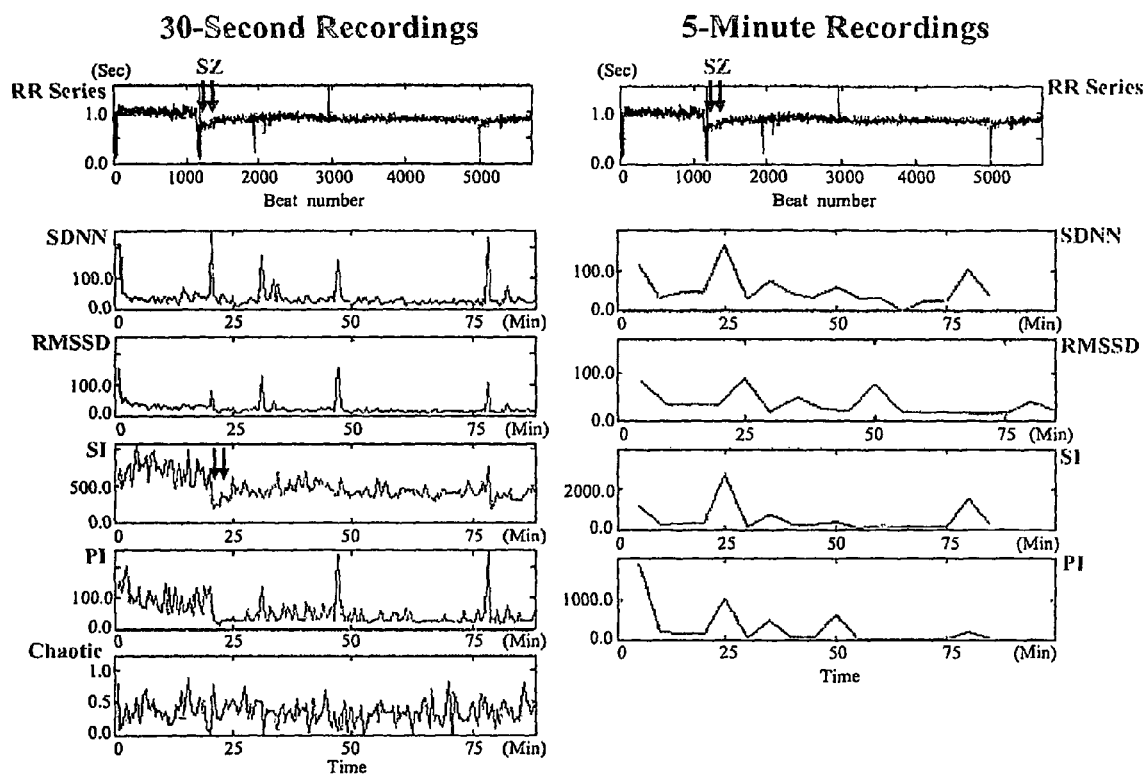
Figure 11: An example of the results analyzed from the system performing HRV analysis on pre-acquired representative data of an epileptic seizure episode electrocardiogram. SZ denotes time seizure occurs.

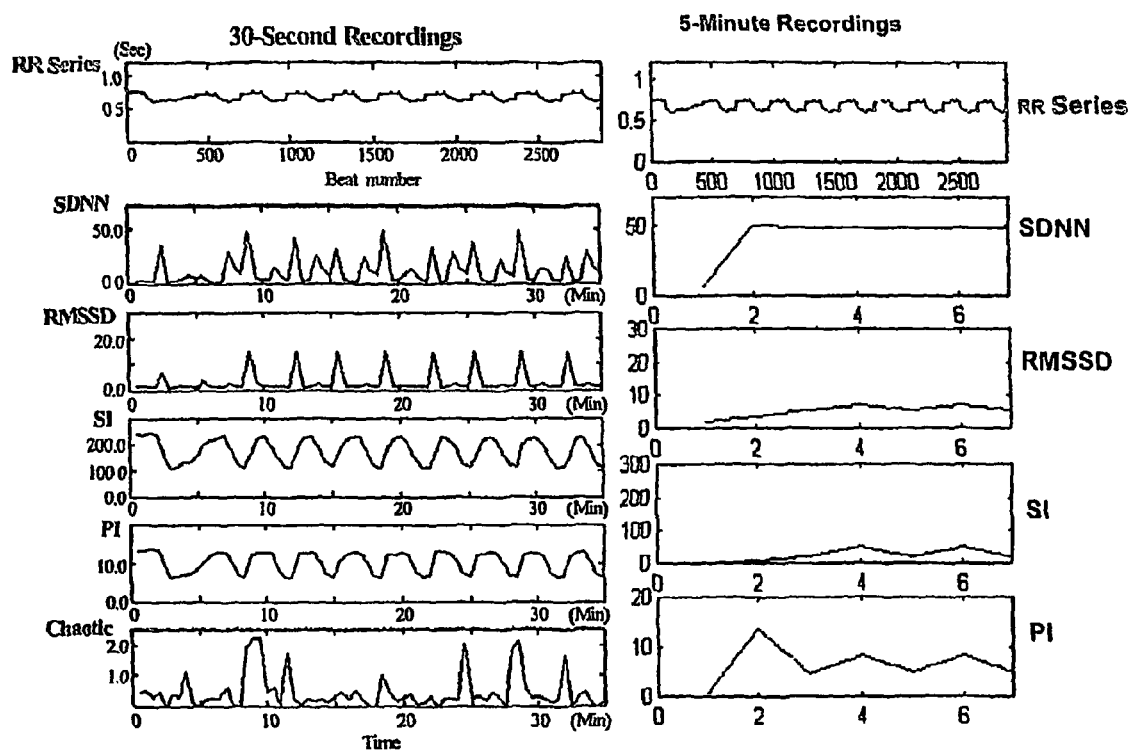
Figure 12: An example of the results analyzed from the system performing HRV analysis on pre-acquired representative data for an electrocardiogram of a sedated baboon.

INSTANTANEOUS AUTONOMIC NERVOUS FUNCTION AND CARDIAC PREDICTABILITY BASED ON HEART AND PULSE RATE VARIABILITY ANALYSIS

GOVERNMENT SUPPORT

The present invention was made with U.S. Government support from the National Institutes of Health, National Heart, Lung, and Blood Institute, under Grant No. HL 67735, and the National Institute of Neurological Diseases and Stroke, under Grant No. NS 37981. The U.S. Government has certain rights in this invention.

FIELD OF THE INVENTION

The present invention relates to the provision of analytical techniques for detecting instantaneous autonomic nervous function and cardiac predictability using non-invasive measurements, and more particularly to immediate processing, analysis and display of the time course of the heart rate variability data and its surrogates using non-stationary and non-linear heart rate variability analysis.

BACKGROUND

Measurements of heart rate and its variability are well known in the art for their usefulness in assessing the conditions of the cardiac and the autonomic nervous systems (ANS) in both health and in disease. They are useful for monitoring many chronic diseases, such as diabetes and heart failure, as well as for monitoring cardiac status during exercise. Particularly useful is Heart Rate Variability (HRV) analysis, which is a non-invasive, clinical tool for assessing the autonomic regulation of cardiac activity as well as various autonomic-related conditions. The ANS has sympathetic and parasympathetic components. The separate rhythmic contributions from sympathetic and parasympathetic autonomic activity modulate heart rate, and thus the R-R intervals of the QRS complex in the electrocardiogram (ECG), at distinct frequencies. In humans, sympathetic activity is associated with the low frequency range (0.04-0.15 Hz) while parasympathetic activity is associated with the higher frequency range (0.15-0.4 Hz.) of the heart rate. This difference in frequency ranges allows HRV analysis to separate sympathetic and parasympathetic contributions.

educed HRV has been associated with such problems as higher long-term risk of post-infarction mortality while changes in the magnitude of, and balance between the two major components of the ANS (the sympathetic and the parasympathetic nervous systems) have been associated with diabetic neuropathy, sleep apnea, syncope and epilepsy.

Such HRV analysis has heretofore typically been performed by monitoring a subject's heart activity and storing the data from the monitored heart activity. The heart activity is monitored for several minutes to several hours. HRV analysis is commonly performed by measuring the beat-to-beat interval between successive heartbeats as collected on an electrocardiogram (ECG). A particularly useful parameter is the period between succeeding "R" waves (the RR interval), where "R" is the conventional designation given the waveform peak of a normal heartbeat as illustrated in FIG. 1. The data are transferred to a computer in which they are analyzed to provide the investigator with information such as the BPM (beats per minute [Heart Rate or Pulse Rate]), SDNN (standard deviation of RR intervals [or inter-pulse intervals] derived from the electrocardiogram [or pulse] data after putative abnormal RR intervals [or inter-pulse intervals] are removed), and RMSSD (root-mean-square of the difference between successive RR intervals [or inter-pulse intervals] derived from the electrocardiogram [or pulse] data). The generated information is reviewed by the investigator, typically long after the heart activity which was used to generate the information has taken place, and the investigator uses the generated information at that later time to determine a status or, in the case of a physician, to develop a treatment procedure for the patient. Task Force of the European Society of Cardiology and the North American Society of Pacing and Electrophysiology. *Heart Rate Variability: Standards of Measurement, Physiological Interpretation, and Clinical Use.* Circulation, 93(5), pp 1043-1065, 1996; Goldberger A L, Amaral L A N, Glass L, Hausdorff J M, Ivanov PCh, Mark R G, Mietus J E, Moody G B, Peng C K, Stanley H E. PhysioBank, PhysioToolkit, and Physionet: *Components of a New Research Resource for Complex Physiologic Signals*. Circulation 101(23): e215-e220 and U.S. Pat. Nos. 5,265,617, 5,437,285, 5,682,901, 5,842,997, 5,957,855, 6,115,629, 6,416,471, 6,480,733, and 6,485,416 variously teach HR monitoring and analysis, and their full disclosures are hereby incorporated by reference.

Many analyses of short-term electrocardiograms use conventional frequency domain HRV techniques (e.g., power spectral density) that assume "stationarity" of the underlying RR interval time series. However, most physiological signals, including heart rate (HR) and pulse rate (PR), are non-stationary by nature. This non-stationarity is a result of complex dynamic interactions among multiple bioregulatory control mechanisms responsible for maintaining homeostasis in the presence of constantly varying physiological and environmental inputs. Additionally, conventional spectral analysis methods are limited by their inability to assess transient changes in HR and PR associated with autonomic reflexes and many rapid changes induced by temporary physical or mental stresses, cardiac, or autonomic nervous system pathologies.

Joint time-frequency (t-f) signal processing techniques may be advantageously used over conventional tools for HRV analysis, given their ability to analyze time-varying spectral properties of non-stationary signals such as HRV. Such t-f techniques are ideally suited for time-localized spectral characteristics of transient cardiac events which occur as a result of temporal changes in the sympatho-vagal activities and balance. The common use of the Gabor spectrogram, where a Fourier transform is calculated for a short-time window chosen to be appropriate for the data to be collected, may make it difficult to achieve an appropriate compromise between frequency resolution and time resolution, especially at times approaching the period of the underlying oscillations.

As noted, physiological systems and their functions continuously respond to challenges. The heart rate varies from beat-to-beat. Such variations are due at least in part to the rhythmic modulation of the heart rate by the autonomic nervous system. However, the assessment of the autonomic nervous system's behavior from a single analysis of HRV can be very misleading. Assessment of the behavior of the autonomic nervous system requires that the HRV data are not based on just a single measurement, but rather that the time course of the behavior of each of the parasympathetic and sympathetic indices must be calculated within a time frame small enough to resolve the temporal nature of the physiological process under investigation.

Thus, to derive the instantaneous responses of autonomic function embedded in the spectral contents of the HRV, the time window needs to be optimal to capture these transient responses. If the window of observation is too short, the broad band white noise embedded in the spectral contents of the HRV will suppress the signals. If the window of observation is too long, the instantaneous responses will be buried in the analysis. In humans or large animals such as primates and dogs, the heart beat averages one to two beats/second, as compared to smaller animals such as the mouse, which averages 10 beats/second. Thus, it should be appreciated that an optimal timing window exists for this type of nonstationary and nonlinear analyses for different average heart rates, with the maximum size of the window dependent on the frequency components of the HRV spectrum selected for analysis.

Techniques such as chaotic analysis have the ability to assess non-linear, spatio-temporal behavior of such deterministic systems as cardiac activity. Additionally, chaotic analysis has the potential for predictive value in the screening of patients susceptible to lethal arrhythmias. A "chaotic Index" (the largest Lyapunov exponent [measure of degree of chaos] can be calculated using the data represented by the heart rate [or pulse rate] sequence. This numerical "chaotic index" can be used to quantify the degree of non-linear deterministic behavior of cardiac activity. Techniques developed out of chaos theory, such as embedding methods and estimation of Lyapunov exponents, help to unravel the original signal underlying an observed single-variable time series and determine how far into the future it can be predicted. Chaotic systems comprise a class of signals that lies between predictable periodic or quasi-periodic signals and totally irregular stochastic signals which are completely unpredictable. The Lyapunov exponent measures the sensitivity of the system to initial conditions and thus provides a measure to help predict the short-term behavior of the system. The computation of the Lypunov exponent is computationally expensive and time consuming and, until the advent of the said invention, not available for such small times.

As noted, most of the HRV analyses, including chaotic indices, are performed using prerecorded ECG data. Although such an approach has value in the treatment of a patient, the delay in the analyzed data provided to the investigator has clear disadvantages. For example, the receipt of analyzed data by a physician may be so delayed as to cause the initiation of treatment to be disadvantageously delayed. In the worst case, the information may be generated too late to be of help in treating the patient. Also, the review of such information by a clinician hours after the data were collected may make it difficult to correlate the data with other conditions of the patient for which data were not being simultaneously recorded or observed. Also, even when the patient is under observation, the clinician may be unable to temporally correlate many of those observations with the corresponding HRV data. Still further, it should be appreciated that prior art HRV information which has been generated based on a preselected set of data presents only a static picture of a dynamic situation.

The present invention is directed toward overcoming one or more of the problems set forth above.

SUMMARY OF THE INVENTION

Since HRV is an important measure of the condition of the heart and the autonomic nervous system, which could change rapidly, it is particularly important to be able to perform real-time HRV analysis while the heart rate is being measured. No current system is able to perform such detailed HRV analysis and display the time course of each of the indices in real time every 30 sec. The present invention relates to a system and method that can simultaneously acquire electrocardiogram or pulse rate data, dynamically perform time-frequency (t-f) and chaotic analysis in real-time, visually display the results in a convenient graphical format and store the results in a computer file format. The system and method can provide a real-time automated system that combines the non-stationary analysis capability for evaluating cardiac signal histories with the predictive capabilities of non-linear analysis to better monitor and categorize autonomic regulation of cardiac function. This system allows for continuous, real-time monitoring of cardiac function and enables short-term prediction of the autonomic control of cardiac activity.

In one embodiment the present invention relates to a method of determining the details of dynamic autonomic nervous system function from the measured variability of heart activity occurring during a time period approximating the inverse of the lowest frequency component of the heart rate variability chosen for analysis, comprising the steps of sequentially receiving data points of heart activity data over a period of time corresponding to the said time period of the heart activity; evaluating said data points as sequentially received to determine QRS events; outputting said QRS events to a processor as they are sequentially determined; processing said output QRS events using time-frequency, nonlinear, nonstationary analysis methods as they are output to periodically determine autonomic nervous system information, wherein said autonomic nervous system information is based on a selected number of output QRS events corresponding to the said selected time period; periodically redetermining said autonomic nervous system information using at least some subsequently output QRS events; and during said period of time corresponding to the time period of the heart activity, displaying the most recently determined autonomic nervous system information.

In another embodiment the present invention relates to a method of determining the details of dynamic autonomic nervous system function from the measured variability of heart activity occurring during a time period approximating the inverse of the lowest frequency component of the heart rate variability chosen for analysis, comprising the steps of sequentially receiving data points of heart activity data over a period of time corresponding to the time period of the heart activity; evaluating said data points as sequentially received to determine QRS events; outputting said QRS events to a processor as they are sequentially determined; processing said output QRS events using time-frequency, nonlinear, nonstationary analysis methods as they are output to repeatedly determine one or more of a sympathetic index, a parasympathetic index and a chaotic index of a selected group of determined QRS events; and during said period of time corresponding to the time period of the heart activity, displaying the most recently determined one or more of the sympathetic index, parasympathetic index, and chaotic index.

In a further embodiment the present invention relates to a method of determining the details of dynamic autonomic nervous system function from the measured variability of heart activity occurring during a time period approximating the inverse of the lowest frequency component of the heart rate variability chosen for analysis, comprising the steps of sequentially receiving data points of heart activity data over a period of time corresponding to the time period of the heart activity; evaluating said data points as sequentially received to determine QRS events; outputting said QRS events to a processor as they are sequentially determined; processing a selected number of QRS events to determine a time-frequency distribution, wherein said determined time-frequency distribution is updated using the most recently output selected number of QRS events; processing the most recently determined time-frequency distribution to determine its spectral power in a low frequency range and its spectral power in a high frequency range of the t-f distribution; and displaying the most recently determined spectral power in the low frequency range and the spectral power in the high frequency range.

In yet a further embodiment the present invention relates to a method of determining the details of dynamic autonomic nervous system function from the sympathetic index, the parasympathetic index, and the chaotic index determined from the measured variability of heart activity occurring during a time period approximating the inverse of the lowest frequency component of the heart rate variability chosen for analysis, comprising the steps of sequentially receiving data points of heart activity data over a period of time corresponding to the time period of the heart activity; evaluating said data points as sequentially received to determine QRS events; outputting said QRS events to a processor as they are sequentially determined; processing said output QRS events using nonlinear, nonstationary methods as they are output to repeatedly determine one or more of a sympathetic index, a parasympathetic index, and a chaotic index of a selected group of determined QRS events; during said period of time corresponding to the time period of the heart activity, displaying the most recently determined one or more sympathetic index, parasympathetic index, and chaotic index; processing a selected number of QRS events to determine a time-frequency distribution, wherein said determined time-frequency distribution is updated using the most recently output selected number of QRS events; displaying the most recently determined time-frequency distribution; processing the most recently determined time-frequency distribution to determine its spectral power in a low frequency range and its spectral power in a high frequency range of the t-f distribution; and displaying the most recently determined spectral power in the low frequency range and the spectral power in the high frequency range.

A system for determining the details of dynamic autonomic nervous system function from the measured variability of heart activity occurring during a time period approximating the inverse of the lowest frequency component of the heart rate variability chosen for analysis, comprising: a heart activity data acquisition device adapted to acquire sequential data points of heart activity of a patient; memory adapted to store sequential data points of heart activity in pre-acquired data files; a user input for selecting between said acquisition device and a selected pre-acquired data file as a data source; a processor adapted to sequentially receive data points of heart activity data from said selected data source, over a period of time corresponding to the said time period of the heart activity, determine QRS events from said data points as sequentially received, output said QRS events as they are sequentially determined, utilize nonlinear nonstationary methods to repeatedly determine one or more of a sympathetic index, a parasympathetic index, and a chaotic index of a selected group of determined QRS events as they are output, determine a time-frequency distribution, wherein said determined time-frequency distribution is updated using the most recently output selected number of QRS events, and for the most recently determined time-frequency distribution, determine spectral power in a low frequency range and its spectral power in a high frequency range; and a display continuously updated during said period of time corresponding to the time period of the heart activity to display the most recently determined one or more sympathetic index, parasympathetic index, and chaotic index, the most recently determined time domain parameters, the most recently determined time-frequency distribution, the most recently determined spectral power in the low frequency range, and the most recently determined spectral power in the high frequency range.

BRIEF DESCRIPTION OF THE DRAWINGS

FIG. 1 illustrates a waveform of a conventional heart beat;

FIG. 2 is an example of a computer and data acquisition device which may be used in accordance with the present invention;

FIG. 3 is an example of a monitor screenshot from the system performing HRV analysis on pre-acquired representative data for a normal electrocardiogram;

FIG. 4 is a flowchart illustrating the overall process of data acquisition, analysis and display of the real-time HRV or pulse rate variability (PRV) analysis system according to the present invention, where FIGS. 5-9 are detailed flowcharts of portions of the FIG. 4 process:

FIG. 5 is a flowchart illustrating the initiation of analysis and data acquisition;

FIG. 6 is a flowchart illustrating details of the event detection step;

FIG. 7 is a flowchart illustrating details of heart rate resampling and RR sequence generation;

FIG. 8 is a flowchart illustrating details in the determination of time-frequency distribution;

FIG. 9 is a flowchart illustrating details of non-linear data analysis;

FIG. 10 is the results analyzed from the system performing HRV analysis on pre-acquired representative data for an electrocardiogram of a subject with sleep apnea;

FIG. 11 is the results analyzed from the system performing HRV analysis on pre-acquired data representative of an epileptic seizure episode electrocardiogram; and FIG. 12 is the results analyzed from the system performing HRV analysis on pre-acquired data representative of a sedated, healthy baboon.

The accompanying drawings, which are incorporated in and form a part of this specification, illustrate embodiments of the invention and, together with descriptions, serve to explain the principles of the invention. They are not intended to limit the scope of the invention to the embodiments described. It is appreciated that various changes and modifications can be made without departing from the spirit and scope of the invention as defined in the appended claims.

DETAILED DESCRIPTION OF THE INVENTION

FIG. 2 illustrates a device which may be used in accordance with the present invention. As illustrated, the device comprises a suitable processing unit, such as a personal computer 12 with a suitable CPU, a user input device 14 (such as the illustrated keyboard, and/or other suitable devices such as a mouse, touch-screen, or keypad-controlled graphic user interface), a suitable display device such as a CRT monitor 16, and a suitable data acquisition device 18 which may be attached to a subject to obtain ECG data from the subject's heart.

To facilitate processing of the various elements of HRV analysis which may be performed in real-time in accordance with the present invention, a suitable processor with architecture for performing specific functions may be advantageously used with the computer 12. For example, Intel Corporation's IPP ("Integrated Performance Primitives") for its Pentium® processors and Itanium® architecture permit a variety of operations which are performed in connection with the present invention to be quickly performed, and may therefore be advantageously used in the computer 12 used with the present invention. For example, where Visual C++ based software code is used to perform the operations providing the desired HRV analysis, the following operations may be performed using IPP function calls: memory allocation and deallocation, array initialization, freeing of memory, calculating means, absolute values and exponentials for array elements in multidimensional arrays, Fast Fourier Transforms (FFT) and Inverse FFTs. Use of such IPP function calls permits such functions to be performed with significantly fewer lines of software code than would be required to perform such functions with normal processing, and therefore significantly speeds up the processing functions to allow analysis to stay in real-time as the processes are continuously updated, as discussed in further detail below.

Suitable ECG data acquisition devices 18 acquire heart beat data such as is known in the art, and are available from, for example, QRS Diagnostic, LLC of Plymouth, Minn., U.S.A., which have devices which may be connected directly to a serial port on a PC processing unit without requiring special hardware to communicate through the serial port. However, it should be understood that many different data acquisition devices may also be advantageously used within the scope of the invention including, for example, stand alone ECG devices interfaced to a PC via standard analog and digital converter boards, or devices which may be directly connected to different computer ports, such as PCMCIA ports conventionally found in laptop computers. In addition, a battery-powered device, such as a cell phone, PDA, or tablet PC may be used in combination with an electrocardiogram, blood pressure, or pulse sensor, for acquisition, transmission and remote monitoring of heart rate variability or pulse rate variability parameters. Further, it should be recognized that multiple devices may be used with a single computer (whether other computer components or other ECG data acquisition devices), with the connection to the ECG data acquisition device of interest (connected to the subject of interest) being selectable by the user. As another example, it should be appreciated that the present invention may utilize a battery-powered, Class II biofeedback device, such as a PDA or a battery powered computer, in combination with a pulse sensor or ECG acquisition system.

Further, as detailed herein, the data acquisition device 18 may be used in connection with the present invention to provide data for real-time analysis simultaneously with its collection, or may acquire data which are suitably stored (e.g., on the hard drive of a personal computer 12) in a form which preserves moment-to-moment correlative relationships so that they can be retrieved electronically for later playback or as hard copy for later review and/or documentation.

FIG. 3 is an example of a video display on a monitor 16 of the HRV analysis of a normal ECG in accordance with the present invention, where the data being analyzed has been pre-acquired. The video display consists of 4 quadrants:

The first quadrant, the ECG and RR interval identification consists of 4 displays:

Graphic display element 20 illustrates in wave form the unprocessed electrocardiogram or pulse data of the pre-acquired data file;

Graphic display element 21 is the average heart rate or pulse rate derived from the corresponding electrocardiogram or pulse data each and every 30 sec of ECG data;

Graphic display element 22 is the corresponding RR peaks derived from the corresponding electrocardiogram or pulse data every 30 sec;

Graphic display element 23 is the corresponding standard deviation of the normal-to-normal (NN) intervals (SDNN) and the square root of the mean of the sum of the squares of differences between successive NN intervals (RMSSD) derived from the corresponding electrocardiogram or pulse data for every 30 sec;

The second quadrant, containing stationary HRV analysis of ECG or pulse data for every 5 minutes according to the European standard, consists of two displays:

Graphic display element 24 is the SDNN and RMSSD derived from the electrocardiogram or pulse data every 5 min;

Graphic display element 25 is the low frequency (LF) and the high frequency (HF) powers corresponding to the SI and PI indexes derived every 5 min, using stationary power spectrum analysis;

The third quadrant, nonstationary time-frequency analysis, consists of three displays:

Graphic display element 26 is the interpolated RR interval every 30 sec;

Graphic display element 27 is the intensity-mapped time-frequency distribution color contour plot, with its time axis (the horizontal axis) shared with the time axis of display element 26;

Graphic display element 28 is the derived SI, PI and SI/PI ratio every 30 sec, with its time axis (the horizontal axis) indicated;

The fourth quadrant, the nonlinear chaotic analysis, consists of two displays:

Graphic display element 29 is the electrocardiogram or pulse attractor ("ECG attractor") derived from the electrocardiogram or pulse data;

Graphic display element 30 is the chaotic index derived every 30 sec.

There are three displays in addition to the aforementioned four quadrants:

Graphic display element 31 is the play button for pre-acquired data processing (if operated while the data is being acquired from a patient, element 28 functions as a start button);

Graphic display element 32 is the stop button both for pre-acquired data processing and for the mode of operation in which the data is processed real-time as it is acquired from a patient; and Graphic display element 33 is the dialog box for reporting system status.

In the example shown, the heart rate is 83 beats per minute and the chaotic index is 0.72. The SDNN, the RMSSD, the SI/PI ratio and the chaotic index are dynamic and vary over time. When it is used in real time or with a file of pre-acquired data, the analysis and display of the data and analysis occurs dynamically over time corresponding to the passage of time which occurred when the data were acquired. It should also be appreciated that when used as the data are being acquired, as discussed herein, the analysis and display of the data and their analysis occur dynamically as the dynamic event (i.e., subject heart beat) occurs.

FIG. 4 is a flow chart illustrating the dynamic, real time HRV analysis which may be performed in accordance with the present invention. Further details of this operation illustrated in overview in FIG. 4 are set forth hereinafter, including in FIGS. 5-9 and in the associated written specification.

Specifically, at box 40 the user inputs data parameters such as detailed further below. Such data parameters may be used to control the analysis mode and output generation, including whether analysis is to be performed using an external data source (at 42) or a file of pre-acquired electrocardiogram or pulse waveform data (at 44). Such parameters can further include, for example, sampling frequency for real time data acquisition, or selection of the file which has the pre-acquired data of interest. The data to be used (such as unprocessed ECG or pulse data) and the parameters to use in connection with their analysis are then received at box 46. This process is set forth in greater detail in FIG. 5 below.

The unprocessed data at box 46 is sent (as indicated by arrow 48) to a suitable display such as a CRT monitor as illustrated in FIG. 3 for graphic display of the waveform in real time (such as illustrated as graphic display element 20 in FIG. 3).

The data at box 46 are additionally analyzed using the user input parameters in accordance with the present invention. That is, the data may be used at box 52 to generate an ECG attractor (as set forth in greater detail in FIG. 9 below) and then displayed as graphical display element 26 (FIG. 3). This graphical "attractor" can be derived, in real-time, from the raw electrocardiogram or pulse rate signal to visually represent the temporal evolution of cardiac dynamics in multidimensional space. Chaotic systems exhibit complex trajectories that do not converge to a fixed point or cross each other as the trajectories evolve over time, while periodic trajectories follow a cyclical path. The data at box 46 may also be analyzed to detect a QRS event at box 54 from which a RR time sequence or inter-pulse sequence may be generated at box 56 (as set forth in greater detail in FIG. 6 below).

The RR time sequence (or inter-pulse sequence) may be used for further HRV analysis, including determining a chaotic index at box 60 (as described in greater detail in FIG. 9 below), and determining time domain parameters at box 62 such as heart rate or pulse rate, RMSSD and SDNN (as described in greater detail in FIG. 7). All of these time domain parameters may be displayed at box 50 such as illustrated in FIG. 3.

The RR time sequence (or inter-pulse sequence) may further be used at box 64 to generate a heart rate (HR) or pulse rate (PR) time sequence or series (as described in greater detail in FIG. 7 below), which may be sent (as indicated by arrow 66) for display as graphical display element 22 (see FIG. 3). Further, the HR time sequence or series may be used at box 70 for time-frequency (t-f) distribution analysis, including generating and displaying an intensity based color-mapped contour plot (as indicated by arrow 72) and generating (at box 74) and displaying (at box 50) SI, PI and SI/PI indexes (as described in greater detail in FIG. 8 below).

FIG. 5 illustrates the initiation of the analysis mode and data acquisition. Specifically, the user first inputs the analysis mode at box 120, indicating whether operation is to use data being acquired at the time (real time) from a subject, or whether or not to use pre-acquired data.

If pre-acquired data are to be used, decision box 122 proceeds to list the available files of pre-acquired data at box 124, and the user selects the desired file at box 126. If the user wishes to perform the analysis using a sampling frequency which is other than the default sampling frequency indicated at box 138 (e.g., 500 Hz which detects the electrical signals of the heart 500 times per second), s/he may do so at box 130, in which case the sampling frequency may be changed to a different selected value at box 132. This may be required, for example, when the pre-acquired data of the selected file were acquired using a different sampling frequency than the default sampling frequency. Whatever sampling frequency is selected, the data from the selected file of pre-acquired data are then sequentially read at box 134 in time order.

Alternatively, if analysis is to occur as the data are being acquired, a determination may first be made by the user at box 140 as to whether or not the computer port receiving the data from the ECG data acquisition device is connected to the default port (e.g., a computer serial port such as previously described). In that case, if the user does not indicate at box 140 that a port different than the default port (e.g., COM Port 4 or the channel number of an analog-digital converter) is to be used, then processing continues at box 142 with data acquisition occurring through the default port. If the user selects a different port, then the selected different port is set at box 144 to be recognized as receiving the data. Once the proper port for receiving data is set, the computer then begins to acquire data at box 146 from the ECG data acquisition device.

As those data are acquired, whether from the computer file of pre-acquired data at a selected sampling frequency (at box 134) or from the ECG data acquisition device (at box 146), the data may at box 148 be displayed on the monitor 16 to show the ECG waveform, which display may be updated periodically (e.g., every 0.1 seconds).

As sequential data are acquired according to the above, processing of the data then proceeds, including event detection 150 (FIG. 5) and non-linear analysis 152 (FIG. 9, discussed further below).

Event detection as illustrated in FIG. 6 involves determination of a QRS event in a sequential set of data points in a time series of ECG data, which may be characterized as data(t). As is recognized by those skilled in the art, the ECG waveform of a standard heartbeat is illustrated in FIG. 1, with the standard peaks in that waveform having the conventional designations P, Q, R, S and T. Detection of a QRS event is the detection of an ECG waveform in the form of points Q, R and S. Engelse, W. A. H., and Zeelenberg, C.: *A Single Scan Algorithm for QRS-Detection and Feature Extraction*. Computers in Cardiology 6, 37-42, 1979 teaches QRS event detection, and the full disclosure thereof is hereby incorporated by reference herein.

Initial filtering of the data first occurs. For example, a differentiator with a 60 Hz notch filter is applied at box 220, $$ECG'(i) = ECG(i) - ECG(i-m) \ (i=1, 2, \ldots N)$$

Where m is the unit of time delay defined as m=fs/60, fs is the sampling frequency of the ECG, and N is the number of data points in the ECG data segment. Such a differentiator filters out power line noise conventionally found at around 60 Hz, as is explained in Friesen, G. M., Jannett, T. C., Jadallah, M. A., Yates, S. L., Quint, S. R., and Nagle, H. T.: *A Comparison of the Noise Sensitivity of Nine QRS Detection Algorithms*. IEEE Transactions on Biomedical Engineering, BME-37 (1), pp 85-98, 1990, the complete disclosure of which is hereby incorporated by reference. In addition to filtering out power line noise, a low pass filter may also be applied at box 222 to filter out high frequency noise, where:

$$ECG''(i) = ECG'(i) + 4ECG'(i-1) + 6ECG'(i-2) + 4ECG'(i-3) + ECG'(i-4)$$

Such a suitable filter is also explained, for example, in Friesen et al.

To precisely annotate the R wave, we search the peak values of the QRS wave between a positive and a negative threshold of equal magnitude. The thresholds are adaptively adjusted for each ECG segment using the equation:

$$TH^j = \alpha \times ECG_{max}^j$$

where $TH^j$ is the threshold of the $j^{th}$ ECG segment, $ECG_{max}^j$ is the maximum value of the $j^{th}$ {ECG"(i), i=1, 2, ... N} segment, and $\alpha$ has a value between 0.35 to 0.45. The {ECG"(i), i=1, 2, ... N} data segment is then scanned for an "onset" point of a QRS wave which is the point where its amplitude is greater than the positive threshold (box 224). From the onset point of the QRS wave, the {ECG"(i), i=1, 2, . . . N} data segment is then continuously scanned for the next 100 ms of the data segment for the "offset" point of a QRS wave (box 230) which is the point where its amplitude is less than the negative threshold (Box 240). The R-wave ficudial point of the QRS complex is the point of maximum magnitude between the "onset" and "offset" of a QRS complex (box 244). Scanning through the complete ECG segment, all R-wave peaks in the ECG segment are determined (box 226).

The difference in time between two adjacent R-wave ficudial points, $T_{RR}$, is defined as $$T_{RR}(n) = \frac{N_{RP}(n+1) - N_{RP}(n)}{f_s}(s)$$

where $T_{RR}(n)$ is the $n^{th}$ RR-interval data in second, $f_s$ is the sampling rate of ECG, $N_{RP}(n+1)$ and $N_{RP}(n)$ are the indices of the sampling points of the $(n+1)^{th}$ and $n^{th}$ R-wave peaks, respectively.

Once all of the current ECG data has been analyzed as determined at box 226 so that a QRS event has been detected, heart rate resampling and RR sequence generation (of the RR time series) proceeds at box 250. The RR time series may then be used in non-linear analysis at box 152 as discussed further below in connection with FIG. 9.

Heart rate resampling and RR sequence generation is illustrated in FIG. 7.

The uneven sampled RR intervals sequence are converted to a continuous time series for frequency domain analysis using a cubic spline interpolation. Briefly, for a RR interval sequence, $\{[T_{RR}(n), T_n], n=1, 2, \ldots N\}$, where N is the number of data points of RR interval sequence of a 30-sec ECG segment, and $T_{RR}(n)$ and $T_n$ are the $n^{th}$ RR-interval value and its corresponding time index, respectively. For each RR interval sequence, the following cubic spline interpolation is applied:

$$S_n(t) = a_n(t-T_n)^3 + b_n(t-T_n)^2 + c_n(t-T_n) + d_n \text{ for } t\epsilon[T_n, T_{n+1}]$$

where $\{a_n, b_n, c_n, d_n\}$ are the 4 coefficients between the time interval $[T_n, T_{n+1}]$. These are governed by 4 independent conditions:

$$S_n(t_n) = T_{RR}(n); S_n(t_{n+1}) = T_{RR}(n+1); S'_{n-1}(t_n) = S'_n(t_n); \text{ and } S''_{n-1}(t_n) = S''_n(t_n)$$

where $S'(t_n)$ and $S''(t_n)$ are the first and second derivatives of the cubic spline interpolation derived from the above equation. For all [N−1] time intervals, there are 4N linear conditions for 4N unknown coefficients. Expressing them in linear matrix notation, we have $$[A][X] = [B]$$

where [X] is the coefficient matrix containing $\{a_n, b_n, c_n, d_n\}$, [A] is a sparse, diagonally dominant and tri-diagonal matrix contains the time indices and the RR intervals and [B] is the matrix contains the corresponding $1^{st}$ and $2^{nd}$ derivatives. Using LU-decomposition, the solution for [X] of the linear matrix shown in the equation for the coefficients $\{a_n, b_n, c_n, d_n\}$ is obtained.

To resample the RR interval sequence, the new time indices with an identical interval are derived from a given resampling rate. For a new time index $t_j^{res}$, with an assumption of $t_j^{res} \epsilon [t_n, t_{n+1}]$, the RR interval value at the new time index is determined by the equation above. Note that the spline interpolation also fills in the missing RR interval data, if any, in the original RR-interval sequence. To adopt the FFT for frequency transforms and joint-time frequency distribution analysis (described below), 256 equal samples of the interpolated RR interval sequence are obtained between each time interval $[T_1, T_N]$ for each 30-sec data segment.

At box 320, the locations of R peaks as data points are identified (based on where QRS events were identified during event detection described above in connection with FIG. 6). With the R peak data points identified, a sampling rate is chosen at box 322 for the heart rate signal (e.g., sampling frequency/100), such as is shown in Berger, R. D., Akselrod, S., Gordon, D., and Cohen, R. J., *An Efficient Algorithm for Spectral Analysis of Heart Rate Variability*. IEEE Transactions on Biomedical Engineering, BME-33 (9), pp 900-904, 1986, the full disclosure of which is hereby incorporated by reference. The number of RR intervals (i.e., the interval from one R peak to the next R peak of a waveform) contained within a local window of the heart rate signal (for every 30 sec) is then generated with identical time interval index (box 324). It is then used to calculate the corresponding interpolated RR interval values at box 326. The RR intervals are then resampled with equal time intervals at box 328 (as displayed element 26 in FIG. 3) and processing of a time-frequency distribution may proceed at box 340.

Two conventional statistical time domain analyses are implemented: the standard deviation of the normal-to-normal (NN) intervals (SDNN) and the square root of the mean of the sum of the squares of differences between successive NN intervals (RMSSD). The SDNN and RMSSD of the RR intervals of each 30 sec are:

$$SDNN(j) = \frac{1}{N-1}\sqrt{\sum_{n=1}^{N}(T_{RR}(n) - \mu)^2}$$

$$RMSSD(j) = \sqrt{\frac{1}{N-1}\sum_{n=1}^{N-1}(T_{RR}(n+1) - T_{RR}(n))^2}$$

where $SDNN(j)$ and $RMSSD(j)$ are the SDNN and RMSSD of the RR interval sequence of the $j^{th}$ 30-sec ECG segment, respectively, N is number of data points of the RR interval sequence, $T_{RR}(n)$ is the $n^{th}$ RR interval, and μ is the mean of the RR interval sequence. Intuitively, SDNN, the square root of the variance, reflects the cyclic components responsible for the variability in that data segment. Variance is also related to the total power of the spectrum. Thus, the RMSSD also reflects the high-frequency variation components in the heart rate.

After SDNN and RMSSD have been calculated at box 354 for 30 sec and 5 min, they are displayed at box 356.

Determination of time-frequency distribution is shown in FIG. 8. Joint time-frequency distributions may be used to depict the time-varying behavior of signals of which the frequency content is of interest. Use of one of the Wigner-Ville family of time-frequency distributions makes it possible to achieve an appropriate compromise between frequency resolution and time resolution. As illustrated in FIG. 8, a uniformly sampled HR time series is obtained at box 420 such as previously described in connection with boxes 320-340 (FIG. 7).

The time-frequency distribution for the RR time series is then calculated at box 426 using the kernel function which is empirically determined to be optimal, such as described in Pola, S., Macerata, A., Emdin, M., and Marchesi, C., *Estimation of the Power Spectral Density in Nonstationary Cardio-Vascular Time Series: Assessing the Role of the Time-Fre-*

*quency Representations (TFR).* IEEE Transactions on Biomedical Engineering, Vol. 43, No. 1, pp 46-49, the complete disclosure of which is hereby incorporated by reference.

The Choi and Williams (Choi, H. I., and Williams, W. J.: *Improved Time-Frequency Representation of Multicomponent Signals Using Exponential Kernels.* IEEE Transactions on Acoustics, Speech, and Signal Processing 37(6), 862-871, 1989, the complete disclosure of which is hereby incorporated by reference.) joint time-frequency reduced interference exponent distribution (ED) was developed to estimate the spectral contents of the HRV. The exponent kernel $$\left(\varphi(v, \tau) = e^{-\frac{v^2\tau^2}{\sigma}}\right)$$

minimizes the effect of the cross-components without violating the properties of mathematical constraints of the joint-time frequency distribution. For a given RR interval sequence $\{T_{RR}(n), n=1, 2, \ldots N\}$ derived from a 30 sec ECG segment, its ED time-frequency distribution is denoted by:

$$ED_{TF}(n, w) = 2 \sum_{k=-M/2}^{M/2-1} W_1(k) \times e^{-j2wk}$$

$$\sum_{l=-N/2}^{N/2} W_2(l) \times \sqrt{\frac{\sigma}{4\pi k^2}} e^{\frac{\sigma(l-n)^2}{4k^2}} \times T_{RR}(l+k)T_{RR}^*(l-k)$$

where σ is the scaling factor for suppressing the cross-components, $T_{RR}^*(n)$ is the complex conjugate of $T_{RR}(n)$, $W_1(k)$ and $W_2(l)$ are the frequency-domain and the time-domain window functions, respectively. In the implementation described herein, the scaling factor is fixed to 1.5, the value of both $W_1(k)$ and $W_2(l)$ rectangle windows is 1. The ranges of the rectangle windows, $W_1(k)$ and $W_2(l)$, are $-M/2 \leq k \leq M/2$ and $-N/2 \leq l \leq N/2$, respectively. To utilize the FFT subroutine to efficiently compute the time-frequency ED of RR interval sequence, the equation is re-arranged by setting $w=\pi v/M$ and re-written as follows:

$$ED_{TF}(n, v) = 2 \sum_{k=-M/2}^{M/2-1} e^{-j2\pi vk/M} \oplus \left[\sum_{l=-N/2}^{N/2} \sqrt{\frac{\sigma}{4\pi k^2}} e^{\frac{\sigma(l-n)^2}{4k^2}} \times T_{RR}(l+k)T_{RR}^*(l-k)\right]$$

where n and v are the time and frequency indices of the ED. From the equation, the time-frequency ED of RR interval sequence is implemented according to the following steps (box 426).

Step 1: Compute the product $T_{RR}(l+k)T_{RR}^*(l-k)$ from a given RR interval sequence, $\{T_{RR}(n), n=1, 2, \ldots N\}$. This results in a matrix $[V]_{M \times N}$.

Step 2: Perform a 1-dimensional (1D) FFT of the product [V] for each time sequence. This results in $[W_1]$.

Step 3: Implement a 2-dimensional (2D) FFT on the 2D matrix $[W_1]$ to obtain the real components of the complex analysis. This results in a 2D matrix, $[W_2]$.

Step 4: Multiply the matrix $[W_2]$ by the exponent kernel, $$\varphi(v, \tau) = e^{-\frac{v^2\tau^2}{\sigma}}.$$

This results in a matrix $[W_3]$.

Step 5: Take a 2D inverse FFT of the 2D matrix, $[W_3]$, and compute the real components of the complex analysis. This results in a time-frequency ED of the RR-interval sequence.

Joint t-f distribution analysis mathematically decomposes the RR time series into time-varying components of the frequency spectra. These frequency-domain calculations result in three main HRV spectral components: very low frequency (VLF), low frequency (LF), and high frequency (HF). The LF component (0.04 to 0.15 Hz) has been associated mainly with sympathetic activity while the HF component (0.15 to 0.40 Hz) has been correlated with parasympathetic activity. There is a constant interplay between these autonomic stimuli to influence HR. The resulting sympatho-vagal balance can be quantified by using the ratio of LF to HF spectral power. In this context, analysis using frequency methods has been found to be a better predictor of physiological changes than time-domain methods.

The low-frequency (LF) and high-frequency (HF) components, as well as their ratio, are derived from the time-frequency ED of each RR interval sequence. The default frequency ranges of LF and HF components for humans are 0.04 to 0.15 Hz and 0.15 to 0.40 Hz, respectively. To be consistent with the measures of the LF and HF power that are usually defined as the absolute values of the power (square of milliseconds), the LF and HF power of the time-frequency distribution of RR interval sequence are computed using the following equations:

$$SI_{LF} = \sum_{n=1}^{N} \sum_{v=LF}^{LF_{max}} (ED_{TF}(n, v))^2$$

and $$PI_{HF} = \sum_{n=1}^{N} \sum_{v=HF_{min}}^{HF_{max}} (ED_{TF}(n, v))^2$$

where $SI_{LF}$ is the power of the LF component with a frequency range of $[LF_{min}, LF_{max}]$, $PI_{HF}$ is the power of the HF component with a frequency range of $[HF_{min}, HF_{max}]$, $ED_{TF}(n, v)$ is the time-frequency distribution of RR interval sequence, and N is the length of the window.

An SI index, PI index and SI/PI ratio may be calculated (and displayed) at boxes 430, 432 and 436. The SI index is the spectral power in the 0.04 Hz to 0.15 Hz low frequency range of the t-f distribution integrated over the entire time duration of the t-f distribution displayed on the computer screen, the PI index is the spectral power in the 0.15 Hz to 0.40 Hz high frequency range of the t-f distribution integrated over the entire time duration of the t-f distribution displayed on the computer screen, and the SI/PI ratio is the ratio of SI spectral power to PI spectral power. The SI/PI ratio is a quantification of the above mentioned sympatho-vagal balance. The SI index, PI index and SI/PI ratio correspond to the moment by moment predominantly sympathetic tone, parasympathetic tone, and sympatho-vagal balance, respectively.

The time-frequency distribution for the RR time series calculated at box 426 may also be color mapped according to spectral power intensities at box 450, and the intensity-mapped color display representing that distribution may be displayed at box 452. The color mapping consists of converting the time-frequency (t-f) distribution values to color-coded intensity maps which have been found to visually illustrate certain data conditions which an investigator may find useful. This color mapping may be accomplished by determining the maximum value (global max) of the t-f distribution for the entire time and frequency range for the RR interval sequence being analyzed. The frequency range may be fixed to limits corresponding to the ranges used for computing SI and PI, namely:

Hf_max=0.4 Hz

Hf_min=0.15 Hz

Lf_max=0.15 Hz

Lf_min=0.04 Hz

These frequency ranges are commonly utilized when analyzing human data. Other frequency ranges may be chosen, especially in animals with faster or slower heart rates.

For the analysis of HRV from 5 min ECG recordings based on the European Standard, both statistical and power spectral analysis algorithms are developed. Both statistical parameters, SDNN and RMSSD, are derived from the RR interval sequence of 5 min recording by the equations presented above. Unlike the power spectral analysis of RR interval sequences of 30 sec recording that is performed with the time-frequency distribution, the power spectral analysis of RR interval sequences of 5 min recording is carried out with the traditional Fourier transform. Given a RR interval sequence $\{T_{RR}(n), n=1, 2, \ldots N\}$ of 5 min recording, a one dimensional FFT of the sequence is taken, and then, the LF and HF power are computed from the Fourier transform of the RR interval sequence, as illustrated in display element 25 in FIG. 3.

Non-linear analysis may also be performed using the RR time series (from box 250, FIG. 6) and data waveform displayed (from box 148, FIG. 5) as illustrated in FIG. 9.

The largest Lyapunov exponent of the RR interval is used as the chaotic index of the cardiac dynamics. Given a 30 sec ECG RR interval sequence $\{T_{RR}(n), n=1, 2, \ldots N\}$, the largest Lyapunov exponent, $L_{max}$, is determined based on the Wolf's algorithm described as follows:

Step 1: The RR interval sequence $\{T_{RR}(n), n=1, 2, \ldots N\}$ is normalized to its mean and standard deviation, $$x_{RR}(n) = \frac{T_{RR}(n) - \mu}{\sigma} \quad (n = 1, 2, \ldots N)$$

where $\mu$ and $\sigma$ are the mean and standard deviation of the RR interval sequence, respectively.

Step 2: An m-dimensional 'phase' vector is reconstructed with delay coordinates. With the delay time set to $\tau$, the phase vector, a point on the attractor of the RR interval sequence is defined as:

$$X_{RR}^{(m,\tau)}(n) = [x_{RR}(n), x_{RR}(n+\tau), \ldots, x_{RR}(n+(m-1)\tau)]$$

where m and $\tau$ are 3 and 1, respectively.

Step 1 and 2 are performed at box 530.

Step 3: The minimum Euclidean distance of the nearest neighbor to its first point $X_{RR}^{(m,\tau)}(1)$ is then located. The Euclidean distance between these two points is denoted as $L_1$.

A pair of points, $X_{RR}^{(m,\tau)}(1)$ and its nearest neighbor of $X_{RR}^{(m,\tau)}(t_1)$, is established as the "points of beginning" for the search procedure of $L_{max}$.

Step 4: A pair of evolved points $\{X_{RR}^{(m,\tau)}(1+EVOLV), X_{RR}^{(m,\tau)}(t_1+EVOLV)\}$ are determined from the points of beginning, $\{X_{RR}^{(m,\tau)}(1), X_{RR}^{(m,\tau)}(t_1)\}$, where EVOLV is the time propagated between the beginning points and the evolved points. The Euclidean distance between the pair of the evolved points is computed and denoted as $L'_1$. These are the fiducial points.

Step 5: The search procedure is then repeated from the fiducial points $X_{RR}^{(m,\tau)}(1+EVOLV)$ to the previous phase vector $X_{RR}^{(m,\tau)}(N)$ until a point that satisfies the following two criteria has been found:
(i) $\alpha > L_2 > \beta$, where $L_2$ is the distance between the "newly found point" and the fiducial point, $\alpha$ and $\beta$ are the constants of the boundary values of $L_2$.
(ii) $\theta < \theta_1$, where $\theta$ is the angle between the line joining the 2 previous fiducial-point and the line joining the fiducial point to the "newly found point", and $\theta_1$ is the upper boundary value of $\theta$.

Step 6: The "newly found point" that satisfies these 2 criteria is defined as the nearest point of the next point $(X_{RR}^{(m,\tau)}(1+2*EVOLV))$ on the fiducial trajectory. The searching procedure (from step 4 onwards) is repeated until the fiducial trajectory has traversed the entire data set of the RR interval sequence.

Step 7: $L_{max}$ is then computed as $$L_{max} = \frac{1}{M} \sum_{k=1}^{M} \log_2 \frac{L'_k}{L_k}$$

where M is the totally iterative number of the researching procedure.

Steps 4, 5, and 7 are performed at boxes 532, 534, 536, 538 and 540. The derived chaotic index for every 30 sec is plotted as the time axis of the time series data at box 542.

Specifically, one analysis which may be performed is to use the data point time series for the waveform, whether received from the ECG device or a pre-acquired data file (from box 148, FIG. 5), to generate at box 522 an XY scatter plot conventionally known as an "ECG attractor". As is known to those skilled in the art, the original ECG time series (i.e., data(t)) is used as the Y-coordinate and its time-embedded equivalent time series (i.e., data(t-tau)) is used as the X-coordinate, where tau equals two ECG sample intervals. That is, a delay filter is used to generate the nth dimension of data from the (n−1) dimension. In the illustrated example, a static delay of two sample intervals is used to generate the second dimension, although it should be understood that this can be extended to more dimensions and different delays. The XY scatter plot of the ECG attractor is displayed at box 524.

In another similar non-linear analysis (using the RR time series from box 250, FIG. 6, whereas the graphical representation of the ECG attractor of box 522 uses the raw ECG waveform from box 148, FIG. 5), a two-dimensional XY time series characterized as an RR attractor is generated at box 530 using the RR time series as the Y-coordinate and its time embedded equivalent time series as the X-coordinate, with a time delay equal to two RR sample intervals. The nearest neighbor and its separation from the initial point is then determined at box 532. If the spatial separation is determined at box 534 to be greater than a selected threshold, then Gram-Schmidt reorthonormalization is performed at box 536 on the vector defined by the two points and then the step of box 532 is repeated until the separation does not exceed the threshold for renormalization (as determined at box 536), at which point the principal axis vector can be obtained at box 538. The principal axis vector may then be used at box 540 to estimate the largest Lyapunov exponent, conventionally known as the "chaotic index", which is a measure of the degree of chaos. Algorithms for calculating chaotic index are known in the art, such as shown in Wolf M M, Varigos G A, Hunt D, Sloman, J G. *Sinus arrhythmia in acute myocardial infarction*. Med. J. Aust., 2 pp 52-53, 1978, the complete disclosure of which is hereby incorporated by reference.

The chaotic index may then be displayed at box 542. Determining and periodically monitoring the Lyapunov exponent for a physiological system over an extended length of time could reveal additional trends towards less or more chaotic behavior which may be indicative of a progressive disease requiring pharmaceutical or therapeutic intervention or an adjustment to a treatment regimen.

In accordance with the present invention, the above data analysis may be performed in a dynamic manner by refreshing the analysis in real-time (where real-time is used herein as referring not only to analysis occurring while external data are being received but also to dynamic analysis of pre-acquired data as those data are played back over a time period essentially corresponding to the time period for which the data were previously acquired).

More specifically, as indicated in FIG. 4, the ECG or pulse waveform may be continuously updated to display a waveform at box 50 based on, as an example, the batch of 30 sec data received at box 46. At a 500 Hz sampling frequency (comprising 500 samples per second), those data points are also XY plotted at box 52 and displayed at box 29 and box 524 as the ECG attractor.

Those same data points are also processed for event detection (see FIG. 6) at box 54 of FIG. 4, with a continuous output of detected QRS events used to generate a continuous RR sequence (RR time series) at box 56 of FIG. 4 (see box 250, FIG. 6). With event detection being accomplished within the time frame of the batch of data points being processed (e.g., approximately eight seconds for 4,096 data points at a 500 Hz sampling frequency), receipt and event detection for the next batch of 4,096 data points may be accomplished in real-time (i.e., in keeping with the time element of the data points).

While the event detection may be accomplished with a batch of data points, each detected RR interval may nevertheless be output to box 56 of FIG. 4 (generating the RR time series) as it is detected (i.e., before event detection is completed for all 4,096 data points). Therefore, it should be appreciated that at this point in the continuous processing after box 56 of FIG. 4, analysis will occur using RR intervals as "points" rather than raw data points as used in box 54.

Specifically, the chaotic index may be determined at box 60 of FIG. 4 for every 128 RR intervals as determined at box 56 of FIG. 4. Therefore, once a first 128 RR intervals have been determined, the chaotic index will be calculated (see box 540, FIG. 9) and displayed until another group of 128 RR intervals have been determined, at which point a new chaotic index will be similarly calculated and the displayed chaotic index will change to the newly calculated chaotic index.

The time domain parameters (HR or PR, RMSSD, SDNN) determined at box 62 of FIG. 4 are also calculated using RR intervals as data points. These parameters are first calculated and displayed when 30 sec or five min worth of RR interval data have been accumulated, and then may be recalculated and displayed thereafter every time when every 30 sec or five min of RR interval data point is received. Thus, the SDNN parameter is the standard deviation of RR intervals (or interpulse intervals) derived from either a 30 sec or 5 min time segment of electrocardiogram (or pulse) data, and the RMSSD parameter is the root-mean-square of the difference between successive RR intervals (or inter-pulse intervals) from the same 30 sec or 5 min segment of electrocardiogram (or pulse) data.

Processing beyond box 64 of FIG. 4 uses the HR sequence (HR time series), which is a conversion of the RR time series to a time series having a uniform interval (see box 420, FIG. 8). Those data may then be displayed (per arrow 66) to display 256 uniform interval points accumulated in every 30 sec. The data may similarly be used in such 256 point groupings for time-frequency (t-f) distribution analysis, from which the SI, PI and SI/PI indexes may be calculated at box 72 (see boxes 426-436 of FIG. 8) and then displayed and the t-f distribution spectral power intensities color mapped and displayed (boxes 450-452 of FIG. 8).

It should be recognized that the present invention is not limited to the above details relating to suitable processing of data points, including the particular numbers of points used in individual calculations. However, it should be appreciated that the above described manner of processing the received heart beat data has been found to be suitable in providing the desired real-time analysis, with the attendant advantages to physician knowledge and patient care. It should also be appreciated that instead of patient treatment, the method and system of the present invention could be used for alternative purposes, such as research into the properties of the autonomic nervous system and the consequences resulting from its behavior in both humans and animals.

It should also be appreciated that much of the above may be accomplished using suitable software performing the described processing and display using, for example, the Visual C++ programming language or similar language with comparable power.

FIG. 10 illustrates the results of the HRV analysis performed on pre-acquired representative data for an ECG of a human subject with sleep apnea. During apneic breathing, the RR intervals are increased by 50% with the corresponding SI and PI indexes increased two to three fold, compared to normal breathing. The corresponding 30 sec SDNN and RMSSD followed a similar oscillatory pattern. During normal breathing, the SI and PI indexes are low. There is a marked increase in SI and PI during apneic breathing which returns to basal levels on cessation of apneic breathing. It is notable that the corresponding chaotic index decreased during the series of apneic breathing compared to normal breathing. The 5 minute data analysis of the RR intervals followed a similar trend as the 30 sec data analysis. However, due to the limited temporal resolution of the SDNN, RMSSD, SI and PI indexes when calculated in 5 minute intervals do not conform to the timing of the episodes of apneic breathing, i.e. when it actually occurred and ended.

FIG. 11 illustrates the results of the HRV analysis performed on pre-acquired representative data of an epileptic seizure episode ECG. During normal breathing, the SI and PI indexes gradually decreased to some threshold values where epileptic seizure suddenly occurred. Immediately following the seizure, the RR intervals decreased. The corresponding SI and PI indexes also decreased. These parameters did not return to baseline (pre-seizure time) during the ECG recording session. The corresponding 30 sec SDNN and RMSSD and the chaotic index did not reveal any obvious changes before or after the seizure. Any changes in the 5 minute SDNN, RMSSD, SI and PI indexes did not coincide with the epileptic episode.

FIG. 12 illustrates the results of the HRV analysis performed on pre-acquired representative data for an ECG of a sedated healthy baboon. The RR-series of a sedated baboon exhibited periodic oscillations every 5 minutes. The 30 sec data analysis in terms of the SDNN, RMSSD, SI and PI reveal that they are in phase with the RR oscillations. However, the chaotic indexes, as a predictor of cardiac events, are about 180 degrees out of phase. The 5 minute interval data analysis did not reveal any oscillatory patterns.

The differences in the displayed information between the normal condition of FIG. 3 and the different abnormal conditions of FIGS. 10-11 (the various displayed indexes, as well as the displayed plots [e.g., electrocardiogram, heart rate, intensity-mapped time-frequency distribution color contour plot, electrocardiogram attractor]) and FIG. 12 of a sedated primate provide an important new tool for the development of a detailed understanding of the dynamic mechanisms underlying the conditions represented, and may provide distinct and valuable data to a researcher into the autonomic nervous system or to a treating physician who, when provided in real-time as the patient undergoes the abnormal condition, can be assured of having the most up to date information for evaluation as s/he evaluates possible treatments.

The system and method of the present invention provide a new tool for real-time automated analysis of heart rate variability and its adjuncts, that combines the non-stationary analysis capability for evaluating cardiac signal histories with the predictive capability of non-linear analysis to better monitor and categorize autonomic regulation of cardiac function.

Still other aspects, objects, and advantages of the present invention can be obtained from a study of the specification and the drawings. It should be understood, however, that the present invention could be used in alternate forms where less than all of the objects and advantages of the present invention and preferred embodiment as described above would be obtained.

The invention claimed is:

1. A method of determining the details of dynamic autonomic nervous system function from the measured variability of heart activity occurring during a time period approximating the inverse of the lowest frequency component of the heart rate variability chosen for analysis, comprising the steps of:
   sequentially receiving data points of heart activity data over a period of time corresponding to the said time period of the heart activity;
   evaluating said data points as sequentially received to determine QRS events;
   outputting said QRS events to a processor as they are sequentially determined;
   processing said output QRS events using time-frequency, nonlinear, nonstationary analysis methods as they are output to periodically determine autonomic nervous system information, wherein said autonomic nervous system information is based on a selected number of output QRS events corresponding to the said selected time period; and
   periodically redetermining said autonomic nervous system information using at least some subsequently output QRS events; and during said period of time corresponding to the time period of the heart activity, displaying the most recently determined autonomic nervous system information.

2. The method of claim 1, wherein the said period of time selected is 30 seconds for humans.

3. A method of determining the details of dynamic autonomic nervous system function from the measured variability of heart activity occurring during a time period approximating the inverse of the lowest frequency component of the heart rate variability chosen for analysis, comprising the steps of:
   sequentially receiving data points of heart activity data over a period of time corresponding to the said time period of the heart activity;
   evaluating said data points as sequentially received to determine QRS events;
   outputting said QRS events to a processor as they are sequentially determined;
   processing said output QRS events using time-frequency, nonlinear, nonstationary analysis methods as they are output to repeatedly determine one or more of a sympathetic index, a parasympathetic index, and a chaotic index of a selected group of determined QRS events; and
   during said period of time corresponding to the time period of the heart activity, displaying the most recently determined one or more of the sympathetic index, parasympathetic index, and chaotic index.

4. The method of claim 3, wherein the said period of time selected is 30 seconds for humans.

5. A method of determining the details of dynamic autonomic nervous system function from the sympathetic index, the parasympathetic index, and the chaotic index determined from the measured variability of heart activity occurring during a time period approximating the inverse of the lowest frequency component of the heart rate variability chosen for analysis, comprising the steps of:
   sequentially receiving data points of heart activity data over a period of time corresponding to the time period of the heart activity;
   evaluating said data points as sequentially received to determine QRS events;
   outputting said QRS events to a processor as they are sequentially determined;
   processing said output QRS events using nonlinear, nonstationary methods as they are output to repeatedly determine one or more of a sympathetic index, a parasympathetic index, and a chaotic index of a selected group of determined QRS events;
   during said period of time corresponding to the time period of the heart activity, displaying the most recently determined one or more sympathetic index, parasympathetic index, and chaotic index;
   processing a selected number of QRS events to determine a time-frequency distribution, wherein said determined time-frequency distribution is updated using the most recently output selected number of QRS events;
   displaying the most recently determined time-frequency distribution;
   processing the most recently determined time-frequency distribution to determine its spectral power in a low frequency range and its spectral power in a high frequency range of the time-frequency distribution; and
   displaying the most recently determined spectral power in the low frequency range and the spectral power in the high frequency range.

6. The method of claim 5, wherein said data points of heart activity data are received during the heart activity.

7. The method of claim 5, wherein said data points of heart activity data are received from a pre-acquired file of data points of the heart activity.

8. The method of claim 6, wherein said period of time selected is 30 seconds for humans.

9. A system for determining the details of dynamic autonomic nervous system function from the measured variability of heart activity occurring during a time period approximating the inverse of the lowest frequency component of the heart rate variability chosen for analysis, comprising: a heart activity data acquisition device adapted to acquire sequential data points of heart activity of a patient; memory adapted to store sequential data points of heart activity in pre-acquired data files; a user input for selecting between said acquisition device and a selected pre-acquired data file as a data source; a processor adapted to sequentially receive data points of heart activity data from said selected data source, over a period of time corresponding to the said time period of the heart activity, determine QRS events from said data points as sequentially received, output said QRS events as they are sequentially determined, utilize nonlinear nonstationary methods to repeatedly determine one or more of a sympathetic index, a parasympathetic index, and a chaotic index of a selected group of determined QRS events as they are output, determine a time-frequency distribution, wherein said determined time-frequency distribution is updated using the most recently output selected number of QRS events, and for the most recently determined time-frequency distribution, determine spectral power in a low frequency range and its spectral power in a high frequency range; and a display continuously updated during said period of time corresponding to the time period of the heart activity to display the most recently determined one or more sympathetic index, parasympathetic index, and chaotic index, the most recently determined time domain parameters, the most recently determined time-frequency distribution, the most recently determined spectral power in the low frequency range, and the most recently determined spectral power in the high frequency range.

10. The system of claim 9, wherein processor includes function calls for Fast Fourier Transforms and Inverse Fast Fourier Transforms.

11. The system of claim 9, wherein said period of time selected is 30 seconds for humans.

\* \* \* \* \*

UNITED STATES PATENT AND TRADEMARK OFFICE
CERTIFICATE OF CORRECTION

PATENT NO. : 7,933,644 B2
APPLICATION NO. : 10/552009
DATED : April 26, 2011
INVENTOR(S) : Lid B. Wong et al.

It is certified that error appears in the above-identified patent and that said Letters Patent is hereby corrected as shown below:

Column 10, Line 63:

Reads: $TH^j = \alpha \times ECG_{max}{}^j$    Should read: $TH^j = \alpha \times ECG^j{}_{max}$ Column 10, Line 65:

Reads: $ECG_{max}{}^j$    Should read: $ECG^j{}_{max}$

Column 13, Line 36:

Reads: $T_{RR}*$    Should read: $T*_{RR}$

Column 14, Line 36:

Reads: $SI_{LF} = \sum_{n=1}^{N} \sum_{w=LF}^{LF_{max}} (ED_{TF}(n,v))^2$    Should read: $SI_{LF} = \sum_{n=1}^{N} \sum_{w=LF_{min}}^{LF_{max}} (ED_{TF}(n,v))^2$ Signed and Sealed this
Fifteenth Day of November, 2011

David J. Kappos
*Director of the United States Patent and Trademark Office*